(12) United States Patent
McClarren et al.

(10) Patent No.: US 10,188,835 B1
(45) Date of Patent: Jan. 29, 2019

(54) IV STABILIZING DEVICE

(71) Applicants: Karen J. McClarren, North Port, FL (US); Steven M. McClarren, North Port, FL (US)

(72) Inventors: Karen J. McClarren, North Port, FL (US); Steven M. McClarren, North Port, FL (US)

( * ) Notice: Subject to any disclaimer, the term of this patent is extended or adjusted under 35 U.S.C. 154(b) by 152 days.

(21) Appl. No.: 15/388,521

(22) Filed: Dec. 22, 2016

(51) Int. Cl.
*A61M 25/02* (2006.01)

(52) U.S. Cl.
CPC ....... *A61M 25/02* (2013.01); *A61M 2025/026* (2013.01); *A61M 2205/0216* (2013.01)

(58) Field of Classification Search
CPC .... A61M 2205/0216; A61M 2210/083; A61M 2025/026; A61M 25/02; A61M 2025/0213; A61M 2025/0206; A61M 2025/0246; A61M 2025/0253; A61M 2005/1587
See application file for complete search history.

(56) References Cited

U.S. PATENT DOCUMENTS

| | | | |
|---|---|---|---|
| 4,470,410 A * | 9/1984 | Elliott | A61M 5/52 128/877 |
| 4,669,458 A | 6/1987 | Abraham et al. | |
| 5,188,608 A | 2/1993 | Fritts | |
| 5,403,285 A * | 4/1995 | Roberts | A61M 25/02 604/179 |
| 6,464,669 B2 | 10/2002 | Wilke | |
| 7,913,320 B2 | 3/2011 | Grissom | |
| 8,277,419 B1 | 10/2012 | Spitaleri | |
| 9,227,039 B1 | 1/2016 | Williams, Sr. | |
| 2006/0264794 A1 | 11/2006 | Fuchs et al. | |
| 2007/0083163 A1 | 4/2007 | Rydell | |
| 2008/0071224 A1 | 3/2008 | Forsyth | |
| 2008/0208130 A1 | 8/2008 | Furman | |

* cited by examiner

*Primary Examiner* — Theodore Stigell
(74) *Attorney, Agent, or Firm* — Edward M. Livingston, Esq.; Bryan L. Loeffler, Esq.; Livingston Loeffler, P.A.

(57) ABSTRACT

An IV stabilizing device (1) which may be readily attached to or detached from a patient without the use of adhesives by providing a cuff (2) that fits around a patient's arm or other appendage. A securing aperture (11) is located on a body (3) of the cuff (2) through which an IV (8) is inserted under a portion of the cuff thereby allowing the cuff to hold the IV in place on the patient's appendage so it does not move. A window (7) is located above the securing aperture with a flap cover (9). The flap cover and window provide access to the IV.

10 Claims, 3 Drawing Sheets

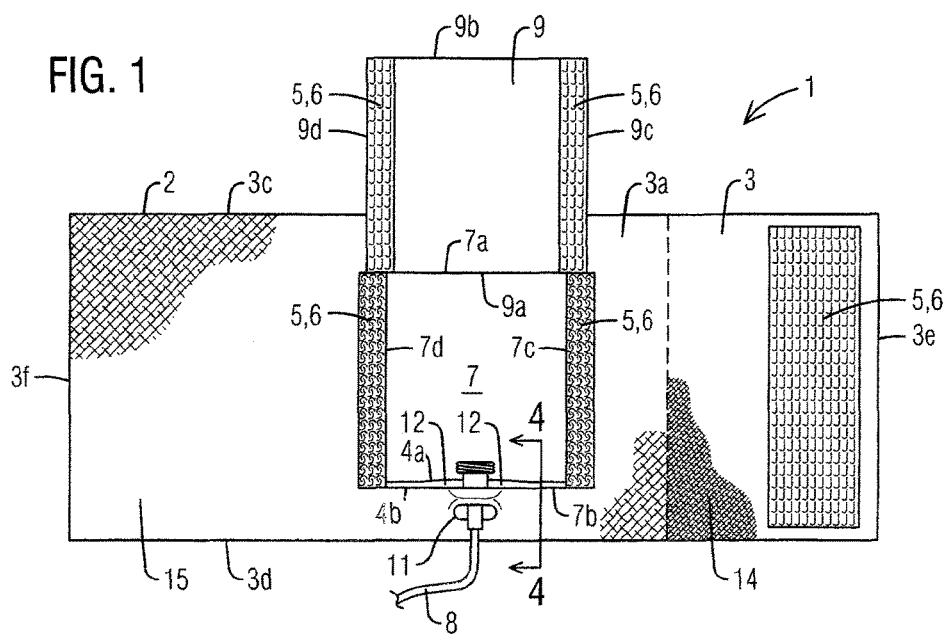
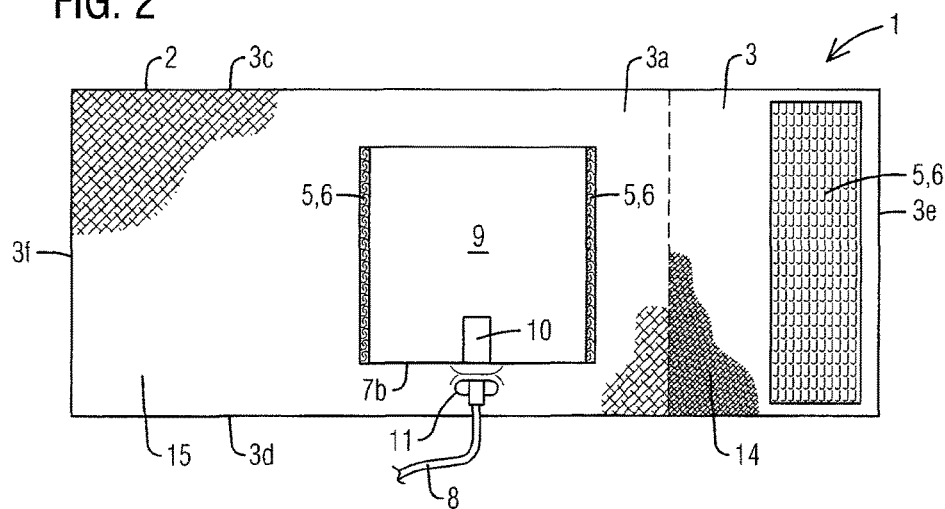
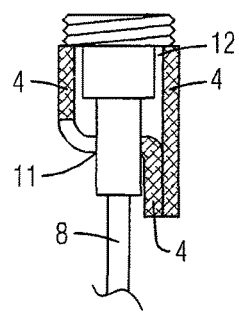

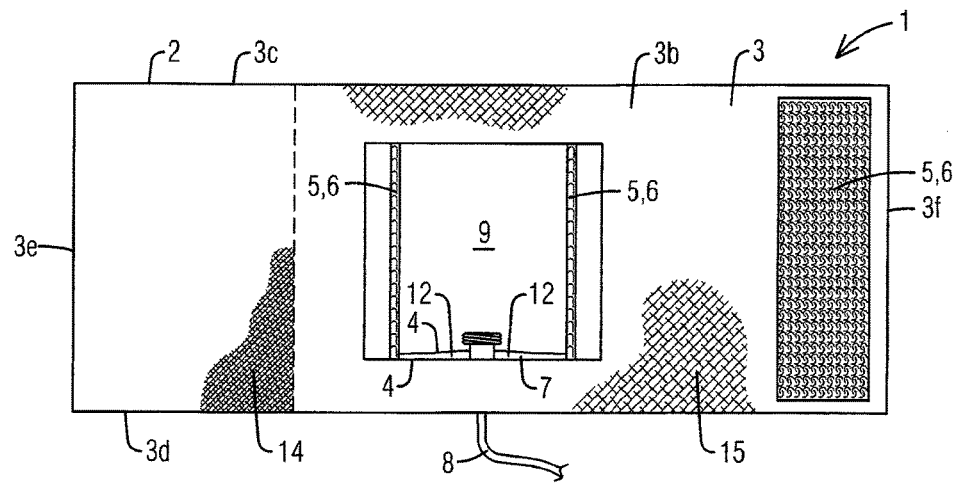
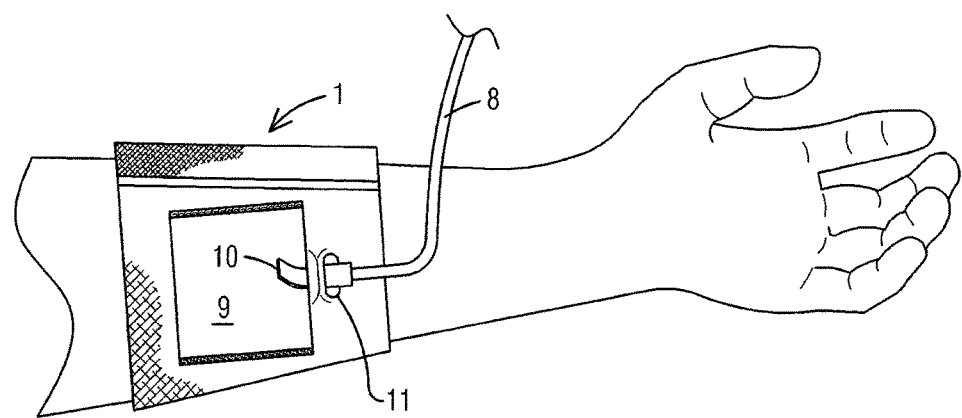

IV STABILIZING DEVICE

FIELD OF THE INVENTION

The present invention relates to intravenous (IV) treatments and more particularly a cuff or other wearable article used for stabilizing and protecting IVs without the use of adhesive tapes.

BACKGROUND OF THE INVENTION

A venipuncture for intravenous treatment can be made in many areas of the human body, such as the forearm, upper arm, leg, hand and so forth. Typically, an IV is inserted into a vein by using a hollow needle which is then withdrawn to avoid damage to the walls of the punctured vein. The IV or needle remains in the vein of the patient and is connected to a source of infusion liquid. It is then necessary to stabilize the IV to prevent movement which may work loose and create a potential source of infection or irritation to the patient at the point of insertion. This stabilization is generally accomplished by taping the IV and associated tube fittings directly to the patient's skin.

Although it is important to obtain secure stabilization of the inserted IV or needle, use of adhesive tape is not always desirable. For example, repeated application and removal of adhesive tape from the skin of a long-term patient and/or elderly patient may damage the skin of the patient and be quite painful. The use of such adhesive tapes is also quite time-consuming, requiring that strips of adhesive tape or similar materials be individually cut and trimmed to fasten the IV directly to the skin of a patient.

Therefore, a need exists for an IV stabilizing device which may be readily attached to or detached from the patient without the use of adhesives.

SUMMARY OF THE INVENTION

The primary object of the present invention is to provide an IV stabilizing device which may be readily attached to or detached from the patient without the use of adhesives.

The present invention fulfills the above and other objects by providing an IV stabilizing device having a cuff that fits around a patient's arm or other appendage and is secured using a fastener, such as a hook and loop fastener. A securing aperture and/or layer opening is located on the body of the cuff through which an IV line is inserted under a portion of the cuff thereby allowing the cuff to hold the IV line in place on the patient's arm so it does not move side-to-side. A window is located above the securing aperture with a flap cover that is held in place by a hook and loop fastener. The flap cover and window provide access to the insertion site of the IV.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF THE DRAWINGS

In the following detailed description, reference will be made to the attached drawings in which:

FIG. 1 is a front view of an IV stabilizing device of the present invention in an open position;

FIG. 2 is a front view of an IV stabilizing device of the present invention in a closed position;

FIG. 3 is a rear view of an IV stabilizing device of the present invention in a closed position;

FIG. 4 is a cross sectional view along line 4-4 of FIG. 1;

FIG. 5 is a view of an anterior view of an IV stabilizing device of the present invention being worn on an arm;

DESCRIPTION OF THE PREFERRED EMBODIMENTS

Figure 6:
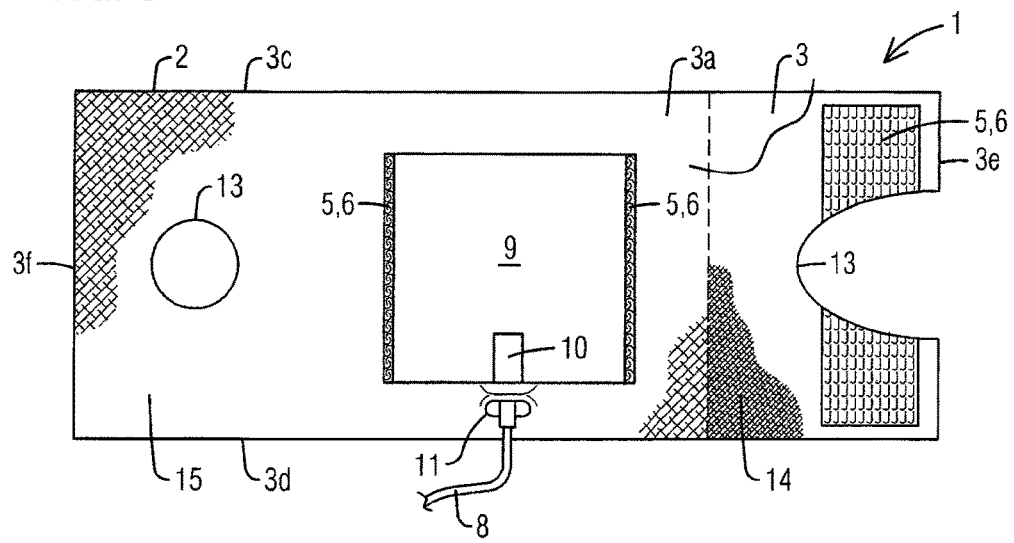
FIG. 6 is a front view of an IV stabilizing device of the present invention in a closed position and having thumb openings.

For purposes of describing the preferred embodiment, the terminology used in reference to the numbered accessories in the drawings is as follows:

1. IV stabilizing device, generally
2. cuff
3. cuff body
3a. front surface of cuff body
3b. rear surface of cuff body
3c. top edge of cuff body
3d. bottom edge of cuff body
3e. right side edge of cuff body
3f. left side edge of cuff body
4. layer
5. fastening means
6. hook and loop
7. window
7a. top edge of window
7b. bottom edge of window
7c. right side edge of window
7d. left side edge of window
8. IV
9. flap cover
9a. top edge of flap cover
9b. bottom edge of flap cover
9c right side edge of flap cover
9d. left side edge of flap cover
10. pull tab
11. securing aperture
12. layer opening
13. thumb opening
14. stretchable material
15. non-stretchable material With general reference to FIGS. 1-7, the IV stabilizing device 1 of the present invention comprises a cuff 2 having a substantially rectangular-shaped body 3 having a front surface 3a, rear surface 3b, top edge 3c, bottom edge 3d, right side edge 3e and left side edge 3f. The cuff 2 may be made of a material having elastomeric properties and have one or more layers 4 making up the body 3. The cuff 2 may be wrapped around a patient's arm or other body part and secured using at least one fastening means 5, such as a hook and loop fastener 6. As illustrated herein, opposing strips of hook and loop fastener 6 are located on the front surface 3a adjacent to the right side 3e of the body 3 and on the rear surface 3b adjacent to the left side 3f of the body 3, thereby allowing the rear surface 3b to be wrapped over the front surface 3a to fasten the cuff 2 in place around a patient's appendage, such as an arm, as illustrated in FIG. 5.

A window 7 is located centrally on the cuff 2 to provide access to the an insertion site of an IV 8 for examination and adjustment if necessary. As illustrated herein, the window 7 comprises a top edge 7a, bottom edge 7b, right side edge 7c and left side edge 7d.

A flap cover 9 covers the window 7 and the insertion site for protection thereof. Said flap cover 9 is substantially the same shape as the window 7, having a top edge 9a, bottom edge 9b, right side edge 9c and left side edge 9d. At least one edge of the flap cover 9 may be permanently attached to an edge of the window 7 to allow the flap cover 9 to be folded back away from the window 7 to reveal the insertion site, as illustrated in FIG. 1. The flap cover 9 attaches to the body of the cuff via at least one fastening means 5, such as a hook and loop fastener 6, to hold the flap cover 9 in a closed position, as illustrated in FIG. 2. As illustrated herein, opposing strips of hook and loop fastener 6 are located on the bottom edge 7b, right side edge 7c and left side edge 7d of the window 7 and bottom edge 9b, right side edge 9c and left side edge 9d of the flap cover 9, respectively. A pull tab 10 is located on the bottom edge 9b of the flap cover 9 to allow for easy removal of the flap cover 9 from the window 7.

At least one securing aperture 11 is located on the body 3 of the cuff 2 adjacent to an edge of the window 7. As illustrated herein, a securing aperture 11 is located between the bottom edge 7b of the window 7 and the bottom edge 3d of the body of the cuff 3.

The securing aperture 11 may pass through the front surface 3a of the body 3 of the cuff 2 and the rear surface 3b of the body 3 of the cuff 2, thereby causing an IV 8 to make contact with a patient's skin when the cuff 2 is wrapped around the patient's arm or other body part to secure the IV 8 in place. The IV 8 is held in place by at least one layer 4 of the cuff 2 under a portion of the cuff 2 located between the securing aperture 11 and an edge of the window 7.

All or a portion of the body 3 of the cuff 2 may comprise two or more layers 4 of material wherein the IV 8 passes through a securing aperture 11 located on a top layer 4a, then between the top layer 4a and a bottom layer 4b, and exit a layer opening 12 located on the bottom edge 7b of the window 7, as illustrated herein. Alternatively, the IV 8 may pass through a securing aperture 11 located on the bottom layer 4b, then between the top layer 4a and the bottom layer 4b, and exit the opening 12 located on the bottom edge 7b of the window 7. In these configurations, the IV 8 is sandwiched between the top layer 4a and the bottom layer 4b when the cuff 2 is wrapped around the patient's arm or other body part. The IV 8 is held in place by at least one layer 4 of the cuff 2 under a portion of the cuff 2 located between the securing aperture 11 and an edge of the window 7. More than one layer opening 12 may be located on the cuff to allow an IV 8 to be inserted through an edge of the cuff body 3 between the layers 4 and out of an a layer opening 12 located on an edge of the window 7.

The rectangular-shaped body 3 may have a portion of non-stretchable material 15 and a portion of stretchable material 14. The portion of non-stretchable material 15 preferably surrounds the window 7 to allow the window to lay flat against an individual's skin. And the portion of stretchable material 14 allows the rectangular-shaped body 3 to expand and contract with an individual's movement while still maintaining compression against the individual's skin.

Figure 7:
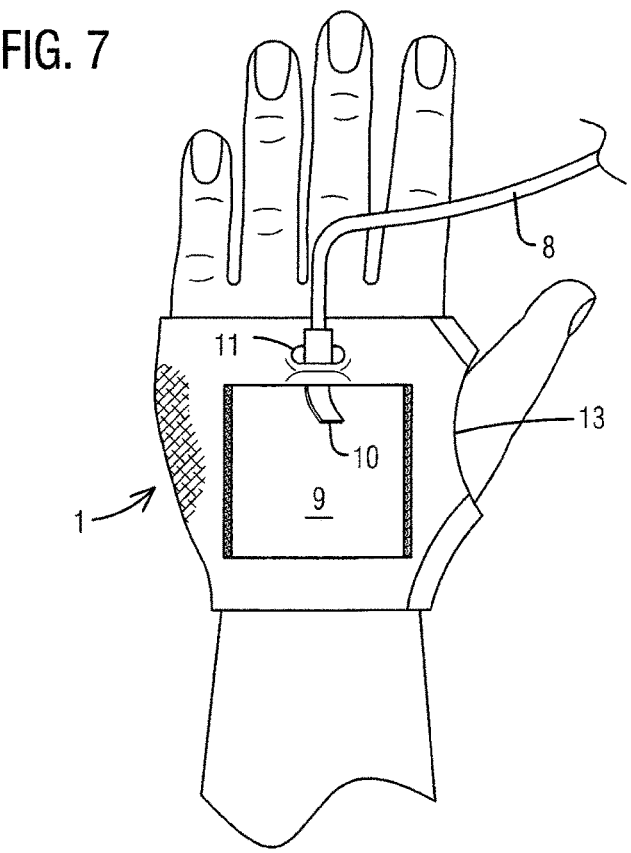
FIG. 7 is a view of a posterior view of an IV stabilizing device of the present invention being worn on a hand.

With reference to FIGS. 6 and 7, the IV stabilizing device 1 of the present invention may also be used on other parts of a patient's body, such as the hand, with little or no modification to the basic design. For example, one or more thumb openings 13, such as a notch, aperture and so forth, may be located on or adjacent to the right side edge 3e and/or the left side edge 3f of the body 3 of the cuff 2. The thumb opening 13 allows the cuff 2 to be wrapped around a patient's hand when an IV 8 is being inserted into the back of the patient's hand.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

We claim:

1. An IV stabilizing device comprising:
   a cuff having a substantially rectangular-shaped body having a front surface, a rear surface, a top edge, a bottom edge, a right side edge and a left side edge;
   at least one fastening means located on the cuff to fasten the right side edge of the body of the cuff to the left side edge of the body of the cuff;
   a window located centrally on the body of the cuff to provide access to an insertion site of an IV;
   a flap cover for covering said window and the insertion site for protection thereof;
   said body of the cuff having a top layer and a bottom layer;
   a securing aperture located on the top layer of the body of the cuff directly adjacent to an edge of the window;
   a layer opening located on the edge of the window which is directly adjacent to the securing aperture; and
   said securing aperture providing access through between the top layer and the bottom layer so that an IV may pass through the securing aperture located on the top layer, then between the top layer and the bottom layer, and exit the layer opening.

2. The IV stabilizing device of claim 1 wherein:
   said flap cover is substantially the same shape as the window.

3. The IV stabilizing device of claim 2 wherein:
   the flap cover is attached to the window to allow the flap cover to be folded back away from the window to reveal the insertion site.

4. The IV stabilizing device of claim 2 further comprising:
   a hook and loop fastener located on the flap cover; and
   a hook and loop fastener located on the body of the cuff to hold the flap cover in a closed position on the window.

5. The IV stabilizing device of claim 1 further comprising:
   at least one thumb opening located on the body of the cuff.

6. An IV stabilizing device comprising:
   a cuff having a substantially rectangular-shaped body having a front surface, a rear surface, a top edge, a bottom edge, a right side edge and a left side edge;
   at least one fastening means located on the cuff to fasten the right side edge of the body of the cuff to the left side edge of the body of the cuff;
   a window located centrally on the body of the cuff to provide access to an insertion site of an IV;
   a flap cover for covering said window and the insertion site for protection thereof;
   said body of the cuff having a top layer and a bottom layer;
   a securing aperture located on the top layer of the body of the cuff directly adjacent to a first edge of the window;
   a layer opening located on the first edge of the window which is directly adjacent to the securing aperture;

said securing aperture providing access between the top layer and the bottom layer so that an IV may pass through the securing aperture located on the top layer, then between the top layer and the bottom layer, and exit the layer opening;

said flap cover is substantially the same shape as the window;

the flap cover is attached to the window to allow the flap cover to be folded back away from the window to reveal the insertion site; and wherein the first edge of the window is located directly opposite of a second edge of the window, the second edge of the window attached to an edge of the flap cover.

7. The IV stabilizing device of claim 6 further comprising:

a hook and loop fastener located on the flap cover; and a hook and loop fastener located on the body of the cuff to hold the flap cover in a closed position on the window.

8. The IV stabilizing device of claim 6 further comprising:

at least one thumb opening located on the body of the cuff.

9. An IV stabilizing device comprising:

a cuff having a substantially rectangular-shaped body having a front surface, a rear surface, a top edge, a bottom edge, a right side edge and a left side edge;

at least one fastening means located on the cuff to fasten the right side edge of the body of the cuff to the left side edge of the body of the cuff;

a window located centrally on the body of the cuff to provide access to an insertion site of an IV, the window comprising a top edge, a bottom edge, a right side edge and a left side edge;

a flap cover for covering said window and the insertion site for protection thereof;

said body of the cuff having a top layer and a bottom layer;

a securing aperture located on the top layer of the body of the cuff directly adjacent to the bottom edge of the window;

a layer opening located on the bottom edge of the window which is directly adjacent to the securing aperture;

said securing aperture providing access between the top layer and the bottom layer so that an IV may pass through the securing aperture located on the top layer, then between the top layer and the bottom layer, and exit the layer opening;

said flap cover is substantially the same shape as the window;

the flap cover is attached to the window to allow the flap cover to be folded back away from the window to reveal the insertion site;

a hook and loop fastener located on the flap cover; and a hook and loop fastener located on the right side edge of the window to hold the flap cover in a closed position on the window; and a hook and loop fastener located on the left side edge of the window to hold the flap cover in a closed position on the window.

10. The IV stabilizing device of claim 9 further comprising:

at least one thumb opening located on the body of the cuff.

\* \* \* \* \*